(12) United States Patent
Walczuch et al.

(10) Patent No.: US 6,727,391 B2
(45) Date of Patent: Apr. 27, 2004

(54) METHOD FOR PROCESSING A LIQUID HYDROFORMYLATION DISCHARGE

(75) Inventors: Karl-Heinz Walczuch, Dürkheim (DE); Rolf Müller, Dannstadt-Schauernheim (DE); Roland Krokoszinski, Weisenheim a.Berg (DE); Bernhard Geissler, Kirchheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/203,293
(22) PCT Filed: Feb. 13, 2001
(86) PCT No.: PCT/EP01/01582
§ 371 (c)(1), (2), (4) Date: Aug. 8, 2002
(87) PCT Pub. No.: WO01/58844
PCT Pub. Date: Aug. 16, 2001

(65) Prior Publication Data
US 2003/0013919 A1 Jan. 16, 2003

(30) Foreign Application Priority Data
Feb. 14, 2000 (DE) .......................................... 100 06 489

(51) Int. Cl.$^7$ ................................................ C07C 45/50
(52) U.S. Cl. ........................ 568/410; 568/438; 568/492
(58) Field of Search ................................. 568/410, 438, 568/492

(56) References Cited

U.S. PATENT DOCUMENTS

| 4,148,830 A | 4/1979 | Pruett et al. ................ 260/604 |
| 4,533,757 A | 8/1985 | Kummer et al. ............. 568/454 |
| 5,883,265 A * | 3/1999 | Tjaden et al. |
| 6,100,432 A | 8/2000 | Borgel et al. ................ 568/454 |

FOREIGN PATENT DOCUMENTS

| EP | 016 286 | 10/1980 |
| WO | 97/07086 | 2/1997 |

* cited by examiner

Primary Examiner—Johann Richter
Assistant Examiner—Sikarl A. Witherspoon
(74) Attorney, Agent, or Firm—Keil & Weinkauf

(57) ABSTRACT

A liquid output from a continuous hydroformylation, which comprises essentially aldehydes, high-boiling by-products, a homogeneously dissolved hydroformylation catalyst, unreacted olefins, low-boiling by-products and dissolved synthesis gas, is worked up by a process in which a) the liquid hydroformylation output is depressurized in a first depressurization stage to a pressure which is from 2 to 20 bar below the reactor pressure, resulting in separation into a liquid phase and a gas phase, and b) the liquid phase obtained in the first depressurization stage is depressurized in a second depressurization stage to a pressure which is lower than the pressure of the first depressurization stage, resulting in separation into a liquid phase comprising essentially high-boiling by-products of the hydroformylation, the homogeneously dissolved hydroformylation catalyst and small amounts of hydroformylation product and unreacted olefin and a gas phase comprising essentially the major part of the hydroformylation product, unreacted olefin and low-boiling by-products.

11 Claims, 1 Drawing Sheet

Fig. 1/1
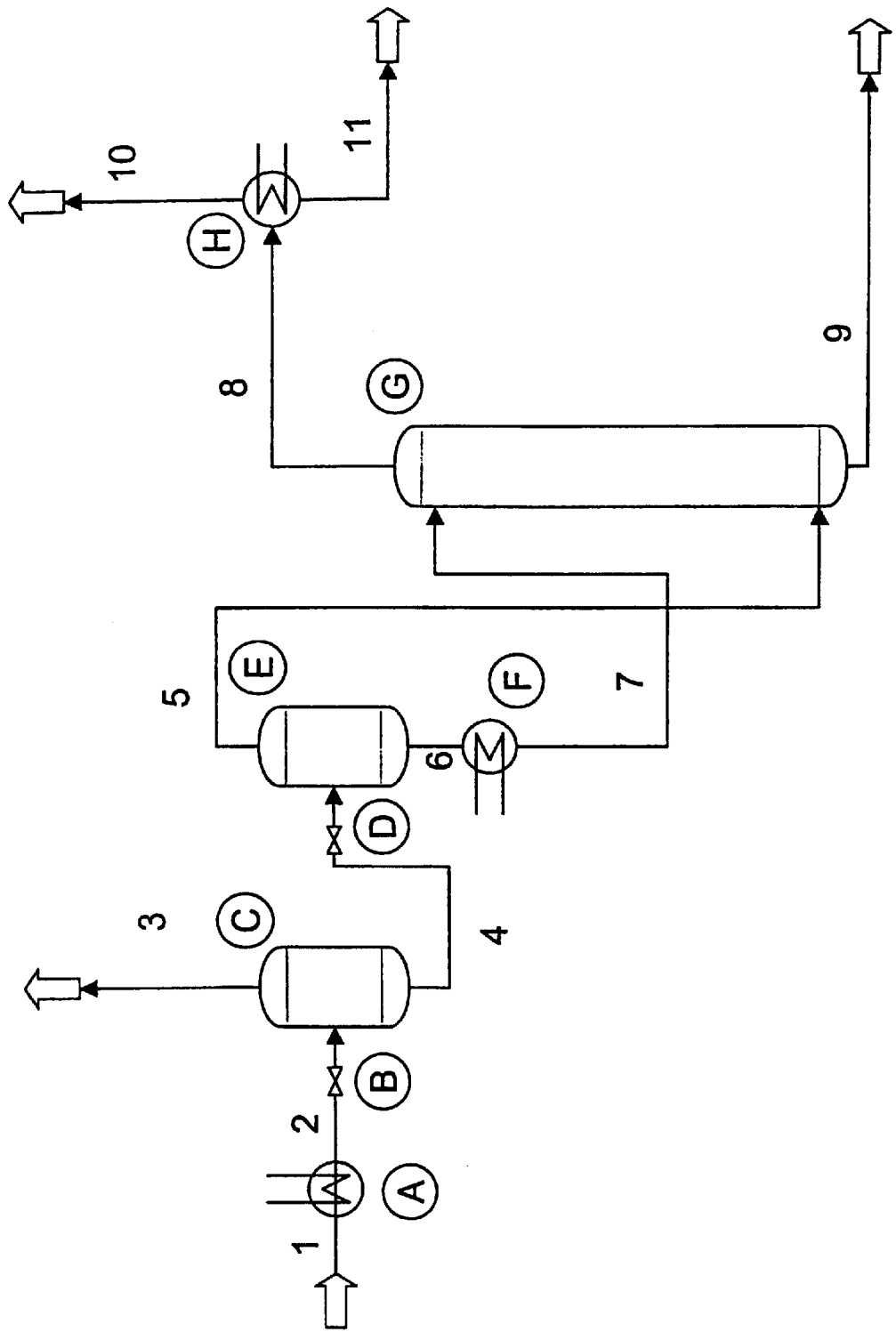

METHOD FOR PROCESSING A LIQUID HYDROFORMYLATION DISCHARGE

The present invention relates to a process for working up a liquid hydroformylation output from a continuous hydroformylation reaction, which output comprises at least one aldehyde as hydroformylation product, unreacted olefins, dissolved synthesis gas, the homogeneously dissolved hydroformylation catalyst and by-products of the hydroformylation reaction.

The hydroformylation of olefins to the corresponding aldehydes is of tremendous economic importance, since the aldehydes prepared in this way are in turn starting materials for many industrial products such as solvents or plasticizer alcohols. Accordingly, there has been a great deal of research worldwide on hydroformylation processes, for example to improve the energy balance of the process, to increase the selectivity and to subject the homogeneous rhodium catalyst to less stress.

The hydroformylation of $C_2$–$C_{20}$-olefins is generally carried out using the liquid output process as is known from EP-A-114 611, U.S. Pat. No. 4,148,830 or EP-A-016 286, in which the essentially liquid output from the hydroformylation reaction is depressurized into an expansion vessel. As a result of the drop in pressure, the output is separated into a liquid phase comprising the catalyst, solvents, high-boiling by-products and a small amount of aldehyde and unreacted olefin and a gas phase comprising the excess synthesis gas together with the major part of the aldehyde formed and of the unreacted olefin. The liquid phase is returned to the reactor as recycle stream and the gas phase is taken off. The gas phase is separated into the synthesis gas plus the unreacted olefins and the aldehyde, which is separated from unreacted olefin by distillation. The synthesis gas and the unreacted olefins are recirculated to the reactor.

WO 97/07086 describes a modified process in which the liquid phase from the expansion vessel is fed into the upper part of a column and the gas phase is introduced into the lower part of the column, so that the liquid phase is treated in countercurrent with the gas phase. This improves the separation of product and high-boiling components. This separation is advantageously carried out at a pressure which is as low as possible so that the separation of product and high boilers can be carried out at temperatures which do not damage the catalyst.

The disadvantage of this process is that large compressors with high energy consumption have to be used in order to compress the excess synthesis gas, unreacted olefins and low-boiling by-products to the reaction pressure and to recirculate them to the reactor.

It is an object of the present invention to provide a more economical process for the hydroformylation of olefins, in which the abovementioned disadvantages in the further work-up of the liquid hydroformulation output from the hydroformylation reactor are circumvented.

We have found that this object is achieved by a process comprising a two-stage flash distillation of the hydroformylation output.

The present invention accordingly provides a process for working up a liquid output from a continuous hydroformylation, which comprises aldehydes, high-boiling by-products, a homogeneously dissolved hydroformylation catalyst, unreacted olefins, low-boiling by-products and dissolved synthesis gas, wherein a) the liquid hydroformylation output is depressurized in a first depressurization stage to a pressure which is from 2 to 20 bar below the reactor pressure, resulting in separation into a liquid phase and a gas phase, and b) the liquid phase obtained in the first depressurization stage is depressurized in a second depressurization stage to a pressure which is lower than the pressure of the first depressurization stage, resulting in separation into a liquid phase comprising essentially high-boiling by-products of the hydroformylation, the homogeneously dissolved hydroformylation catalyst and small amounts of hydroformylation product and unreacted olefin and a gas phase comprising essentially the major part of the hydroformylation product, unreacted olefin and low-boiling by-products.

The process of the present invention is suitable for the work-up of liquid outputs from the rhodium-catalyzed hydroformylation of olefins. Olefins employed are generally ones having from 2 to 20 carbon atoms, in particular from 2 to 10 carbon atoms and particularly preferably from 2 to 5 carbon atoms, or mixtures thereof. The olefins used can be unsubstituted or have one or two substituents which are inert under the hydroformylation conditions, for example an ester group, a nitrile group, an alkoxy group or a hydroxy group.

The rhodium catalysts used are generally complexes which bear one or more organophosphorus compounds as ligands and are homogeneously soluble in the reaction medium of the hydroformylation reaction. Examples of such ligands are phosphine ligands selected from the group consisting of triarylphosphines, in particular triphenylphosphine, $C_1$–$C_6$-alkyldiarylphosphines or arylalkyldiphosphines. Catalysts which can be used are described, for example, in WO 97/07086 and in the patent publications cited therein.

The hydroformylation is generally carried out at from 50 to 150° C. and a pressure in the range from 5 to 50 bar.

At the specified temperature and the specified pressure, the synthesis gas, namely a carbon monoxide/hydrogen mixture having a $CO/H_2$ molar ratio of generally from 20/80 to 80/20, preferably from 40/60 to 60/40, which is used in excess for the hydroformylation is dissolved in the liquid hydroformylation output to an extent corresponding to its solubility. Part of the synthesis gas can be suspended in the hydroformylation output in the form of small gas bubbles.

The liquid part of the output from the hydroformylation reaction comprises, as significant constituents, the rhodium catalyst, the hydroformylation product, i.e. the aldehyde(s) produced from the olefin or olefin mixture used, and also condensation products of these aldehydes which have boiling points higher than that of the hydroformylation product, as can be formed as by-products during the course of the hydroformylation and have been described, for example, in U.S. Pat. No. 4,158,830, together with low-boiling components such as, in particular, the alkanes corresponding to the olefins. The liquid output may further comprise a high-boiling, inert solvent such as toluene or xylene.

The details of the hydroformylation process and the rhodium catalyst used provided above serve to place the process of the present invention in its technical context. It may be pointed out at this point that the hydroformylation preceding the process of the present invention can be carried out by customary liquid output hydroformylation processes known per se from the prior art, for example as described in EP-A-0 16 286, EP-A-188 246 or U.S. Pat. No. 4,148,830.

The liquid hydroformylation output is preferably firstly heated to a temperature which is from 5 to 50° C., preferably from 10 to 30° C., above the reactor temperature. This heating is carried out in the customary manner, generally by means of heat exchangers.

The heated or unheated hydroformylation output is then, in a first depressurization stage, depressurized into a vessel (expansion vessel) to a pressure which is from 2 to 20 bar, preferably from 5 to 15 bar, below the reactor pressure. The pressure in the expansion vessel is then generally in the range from 2 to 40 bar, preferably from 2 to 20 bar.

In the first depressurization stage, the hydroformylation output is separated into a liquid phase and a gas phase. The gas phase comprises essentially excess synthesis gas, unreacted olefin and possibly the alkane corresponding to the olefin. The gas phase is generally, usually after compression to the reactor pressure, recirculated to the reactor. The liquid phase comprises essentially the hydroformylation product, condensation products of the hydroformylation product which have higher boiling points, the catalyst and possibly a solvent such as toluene or xylene.

The liquid phase separated out in the first depressurization stage is then discharged from the expansion vessel as a liquid stream and is, in a second depressurization stage, depressurized into a further expansion vessel to a pressure which is lower than the pressure of the first depressurization stage. The depressurization in the second depressurization stage is preferably to a pressure in the range from 0 to 10 bar, preferably from 1 to 5 bar. The pressure in the second depressurization stage is generally from 2 to 20 bar, in particular from 3 to 15 bar, lower than the pressure in the first depressurization stage.

The liquid phase obtained from the first depressurization stage is separated into a liquid phase and a gas phase in the second depressurization stage. The liquid phase comprises the high-boiling condensation products of the hydroformylation product, the catalyst and possibly solvent and small amounts of hydroformylation products. The gas phase comprises the major part of the hydroformylation product together with residual amounts of synthesis gas and low-boiling components (unreacted olefin and the alkane corresponding to the olefin).

It has surprisingly been found that both the energy consumption and the compressor capacity required for compressing excess synthesis gas and unreacted olefin can be reduced when, as provided for by the present invention, a two-stage depressurization of the hydroformylation output is carried out.

The liquid phase and gas phase obtained in the second despressurization stage can be worked up further by customary methods. For example, the gas phase can be passed to a condenser in which the hydroformylation product, unreacted olefin still present and low-boiling components (first and foremost the alkane corresponding to the olefin) are separated out in liquid form and passed to further purification, e.g. by distillation. The gas phase obtained form the condenser, which comprises essentially the unreacted synthesis gas, unreacted olefin and low-boiling secondary components, can be recirculated wholly or partly to the reactor.

The liquid phase obtained in the second depressurization stage can be recirculated to the reactor either directly or after removal of hydroformylation product still present, e.g. by distillation.

The gas and liquid phases obtained in the second depressurization stage are preferably worked up by the method described in WO 97/07086. For this purpose, the liquid phase is introduced into the upper region of a column while the gas phase is introduced at the bottom of the column. Liquid phase and gas phase are thus treated in countercurrent. To increase the contact between liquid phase and gas phase, preference is given to using a column equipped with random packing elements, e.g. Raschig rings, spirals or saddles, or ordered packing or internals, e.g. trickle trays, in order to create a large surface area. As a result of the intimate contact between the gas phase and the liquid phase, the residual amounts of hydroformylation product and unreacted olefin present in the liquid phase are transferred into the gas phase, so that the gas stream leaving the column at the top is enriched in hydroformylation product and unreacted olefin compared to the gas stream introduced at the lower end of the column. The further work-up of the gas stream leaving the column and of the liquid phase leaving the column is then carried out in a customary manner, for example as described above.

The preferred process of the present invention is described below with the aid of the accompanying drawing using the reference numerals indicated therein. The drawing is purely a schematic flow diagram serving to illustrate the process of the present invention. For reasons of clarity, only the apparatuses necessary for explaining the process have been drawn in, while other self-evident apparatuses necessary for carrying out the process, e.g. pumps, additional valves, instrumentation, etc., have been left out in the drawing. The process of the present invention is not restricted to the embodiment depicted in the drawing.

The hydroformylation output (1) is heated in the heat exchanger (A) to a temperature which is not more than 50° C. above the reactor temperature. The heating of the reactor output is preferred but the process can also be carried out without this heating step. The heated hydroformylation output (2) is depressurized via a valve (B) into the vessel (C) (first expansion vessel). The pressure prevailing in the vessel (C) is generally from 2 to 20 bar below the pressure of the hydroformylation output (1). In the vessel (C), the hydroformulation output is separated into a gas phase comprising the major part of the access synthesis gas, unreacted olefins and low-boiling by-products and a liquid phase. The liquid phase (4) obtained in the vessel (C) is conveyed via the regulating valve (D) into the vessel (E) (second expansion vessel) and depressurized. The depressurization into the vessel (E) results in separation into a liquid phase and a gas phase. The liquid phase comprises essentially the catalyst, relatively high-boiling by-products of the hydroformylation reaction, residual amounts of olefin and of hydroformylation product and possibly a high-boiling solvent used in the hydroformylation. The gas phase comprises essentially the major part of the hydroformylation product and the remainder of unreacted olefin, low-boiling components and unreacted synthesis gas.

The liquid phase (6) separated out in the vessel (E) is taken off and heated by means of a flow heater or heat exchanger (F) to a temperature which is from 10° C. to 80° C. above the temperature of the liquid phase in the vessel (E).

The heated liquid phase (7) from the vessel (E) is conveyed via a line to the top or the top section of the column (G). The gas phase (5) obtained in the vessel (E) is introduced into the bottom of the column (G). The column (G) is a customary column provided with, for example, random packing, ordered packing or internals for intensive gas/liquid exchange. The liquid stream (9) leaving the column (G) at the bottom, which comprises essentially the catalyst and by-products of the hydroformylation reaction having boiling points higher than that of the hydroformylation product, possibly a high-boiling solvent additionally used for the hydroformylation and residual amounts of aldehydes, is recirculated to the hydroformylation reactor (not drawn in on the drawing). The gas stream (8) taken off at the top of the column (G), which comprises the hydroformylation product plus residual amounts of low-boiling components and unreacted olefin and synthesis gas, is conveyed to a condenser (H) where it is cooled and separated into a liquid phase (11) and a gas phase (10). The liquid phase (11) comprises the hydroformylation product and small amounts of unreacted olefin and low-boiling components and is usually passed to a distillation step for further purification. The gas phase (10) comprises the remaining synthesis gas and unreacted olefins and low-boiling secondary components. The gas phase is, after compression to the pressure of the hydroformylation reaction, returned to the hydroformylation reactor. Part of the streams (9) and (10) is advantageously discharged in order to avoid accumulation of interfering secondary components.

The following examples illustrate the invention without limiting its scope.

EXAMPLES

Comparative Example

A reactor for producing 10 kg/h of butyraldehyde from propene, carbon monoxide, hydrogen and rhodium-triphenylphosphine catalyst was operated at 90° C. and a pressure of 20 bar. An amount of 24 kg/h of liquid reactor contents was taken off from the reactor and processed further in an output system as described in WO 97/07086. Compared to the process of the present invention, this process is not preceded by a heat exchanger and a further expansion vessel, i.e. the liquid output (1) is directly depressurized into the vessel (E). Corresponding to the process of WO 97/07086, the liquid output was depressurized into the vessel to a pressure of 1.5 bar.

The depressurization of the liquid hydroformylation output into the expansion vessel (E) resulted in separation of the essentially liquid hydroformylation output into a liquid phase and a gas phase. The liquid phase comprises essentially the catalyst and relatively high-boiling by-products of the hydroformylation reaction, residual amounts of olefin and hydroformylation product. The gas phase comprises essentially the major part of the hydroformylation product, the major part of the unreacted olefin, low-boiling secondary components and unreacted synthesis gas.

The liquid phase separated out in the expansion vessel (E) was taken off as a liquid stream (6) from the expansion vessel via a line and heated by means of a flow heater or heat exchanger (F) to a temperature which was 25° C. above the temperature of the liquid phase of the expansion vessel (E). The liquid stream (7) which had been heated in this way was conveyed via a line to the top section of the column (G). The column (G) was a packed column containing Pall rings and having 5 theoretical plates. The gas phase from the expansion vessel (E) was conveyed as stream (5) to the bottom of the column (G) and thus passed through the column in countercurrent to the liquid stream (7). The liquid stream (9) leaving the column (G) at the bottom via a line, which was depleted in hydroformylation product and unreacted olefin and comprised essentially the catalyst and by-products of the hydroformylation reaction having boiling points higher than that of the hydroformylation product, was wholly or partly returned to the hydroformylation reactor (not drawn in on the drawing). The gas stream (8) taken off at the top of the column (G) via a line, which was enriched in hydroformylation product and unreacted olefin and comprised, as additional significant constituents, saturated hydrocarbons and unreacted synthesis gas, was conveyed for further work-up to a condenser (H) in which the relatively high-boiling constituents, namely the hydroformylation product and small amounts of unreacted olefin and low-boiling components, were separated by condensation from the unreacted synthesis gas. The synthesis gas which had been separated off in this way was compressed to the pressure of the hydroformylation reaction and returned to the hydroformylation reactor.

In this output variant, 1.0 standard cubic meters of gas were obtained after the condensation in the heat exchanger (H). This gas comprised unreacted synthesis gas, propane and propene which had been dissolved in the reactor output. This gas was compressed to the reaction pressure by means of a compressor and recirculated to the reactor.

Example 1

The reactor output (1) was worked up by the process described in the figure, but without use of the heat exchanger (A). A large part (about 40% by volume) of the dissolved gases (sythesis gas, propene and propane) was transferred into the gas phase. These gases were recirculated directly to the reactor. The remaining liquid phase was taken from the vessel (C) and conveyed via a line and the regulating valve (D) into the expansion vessel (E) and treated further as described in the comparative example.

The amount of gas now having to be recompressed downstream of the heat exchanger (H) was reduced from 1.0 to 0.6 standard cubic meters per hour.

Example 2

Example 1 was repeated using the heat exchanger (A) in which the liquid reactor output was heated from 90° C. to 110° C. This resulted in an increase in the amount of gas (3) obtained after the depressurization to about 6 bar (about 60% by volume of the dissolved gases) and recirculated directly from the vessel (C) to the reactor.

The amount of gas now having to be recompressed downstream of the heat exchanger (H) was reduced from 1.0 to 0.4 standard cubic meters per hour.

We claim:

1. A process for working up a liquid output from a continuous hydroformylation, which output comprises aldehydes, high-boiling by-products, a homogeneously dissolved hydroformylation catalyst, unreacted olefins, low-boiling by-products and dissolved synthesis gas, wherein
   a) the liquid hydroformylation output is depressurized in a first depressurization stage to a pressure which is from 2 to 20 bar below the reactor pressure, resulting in separation into a liquid phase and a gas phase, and
   b) the liquid phase obtained in the first depressurization stage is depressurized in a second depressurization stage to a pressure which is lower than the pressure of the first depressurization stage, resulting in separation into a liquid phase comprising essentially high-boiling by-products of the hydroformylation, the homogeneously dissolved hydroformylation catalyst and small amounts of hydroformylation product and unreacted olefin and a gas phase comprising essentially the major part of the hydroformylation product, unreacted olefin and low-boiling by-products.

2. A process as claimed in claim 1, wherein the hydroformylation output is heated to a temperature which is from 5 to 50° C. above the reaction temperature of the hydroformylation prior to the first depressurization stage.

3. A process as claimed in claim 1, wherein the hydroformylation output is depressurized in the first depressurization stage to a pressure in the range from 3 to 40 bar.

4. A process as claimed in claim 1, wherein the liquid phase obtained in the first depressurization stage is depressurized in the second depressurization stage to a pressure in the range from 0 to 10 bar.

5. A process as claimed in claim 1, wherein the liquid phase obtained in the second depressurization stage is introduced into the upper part of a column and the gas phase obtained in the second depressurization stage is introduced at the bottom of the column so that gas phase and liquid phase are treated in countercurrent.

6. A process as claimed in claim 5, wherein the gas phase obtained at the top of the column is separated by condensation into a gas phase which comprises essentially unreacted synthesis gas and unreacted olefin together with the alkane corresponding to the olefin and a liquid phase which comprises essentially the hydroformylation product and small amounts of unreacted olefin and saturated hydrocarbons.

7. A process as claimed in claim 1, wherein the gas phase obtained in the first depressurization stage is recirculated to the reactor.

8. A process as claimed in claim 5, wherein the liquid phase obtained at the bottom of the column is recirculated wholly or partly to the reactor.

9. A process as claimed in claim 7, wherein the gas phase obtained after condensation is recirculated wholly or partly to the reactor.

10. A process as claimed in claim 1, wherein the continuous hydroformylation reactor is carried out using a $C_2$–$C_{20}$-olefin or a mixture thereof.

11. A process as claimed in claim 10, wherein the olefin used is propene.

* * * * *